United States Patent [19]

Dubois et al.

[11] 4,061,682

[45] Dec. 6, 1977

[54] PREPARATION OF SYMMETRICAL ETHERS

[75] Inventors: Robert A. Dubois, Framingham; Harold H. Freedman, Newton Center, both of Mass.

[73] Assignee: The Dow Chemical Company, Midland, Mich.

[21] Appl. No.: 598,529

[22] Filed: July 23, 1975

[51] Int. Cl.$^2$ .............................................. C07C 41/00
[52] U.S. Cl. ............................. 260/611 A; 260/614 R
[58] Field of Search ........................ 260/611 A, 614 R

[56] References Cited

U.S. PATENT DOCUMENTS

| | | | |
|---|---|---|---|
| 3,824,295 | 7/1974 | Gordon | 260/614 R |
| 3,931,238 | 1/1976 | Starks | 260/614 R X |

OTHER PUBLICATIONS

Herriott et al., Tetrahedron, Letters No. 44, (1972), 4521–4524.
McKillop et al., Tetrahedron, vol. 30, (1974), 1379–1382.

*Primary Examiner*—Bernard Helfin
*Attorney, Agent, or Firm*—G. R. Plotecher

[57] ABSTRACT

Symmetrical ethers are prepared in high yield by reacting an alkyl halide, sulfate, or sulfonate with base in the presence of a catalytic amount of both an onium salt and a carboxylate salt. For example, dibenzyl ether is produced in yields exceeding 95 percent by contacting benzylchloride with a 50 percent sodium hydroxide solution in the presence of a catalytic amount of both tetra-n-butylammonium bisulfate and sodium acetate.

12 Claims, No Drawings

PREPARATION OF SYMMETRICAL ETHERS

BACKGROUND OF THE INVENTION

This invention relates to a process for preparing symmetrical ethers.

Many methods are known for preparing symmetrical ethers. Typical references include Houben Weyl, 6/3, pp. 26–30 (1965) and *The Chemistry of the Ether Linkage*, edited by Paul Patai, Interscience Publishers, 1967. The former reference teaches (at pp. 26–27) that symmetrical ethers are prepared by reacting an alkylating agent with an excess of anhydrous alcohol in the presence of a base, while the latter reference teaches (at pp. 446) that said ethers are formed by the reaction of an alcohol with an alkyl halide in liquid ammonia and, alternatively, by the dehydration reaction of alcohols in acid (at p. 457). Both Houben Weyl (at pp. 28–30) and Patai (at p. 446) teach that said ethers are formed by the reaction of a preformed alkali metal alkoxide with an alkylating agent in a dry inert solvent.

The use of quaternary salt catalysts in the production of symmetrical ethers is also known. A. W. Herriott and D. Picker (*Tet. Lett.* 44, p. 4,521 (1972)) teach that the reaction of 1-bromooctane with 2N sodium hydroxide in the presence of a quaternary ammonium salt catalyst produces di-n-octyl ether in 75% yield. R. D. Gordon (U.S. Pat. No. 3,824,295) also teaches that the reaction of an alkyl halide, sulfate or sulfonate with aqueous caustic in the presence of a quaternary salt catalyst produces a symmetrical ether.

SUMMARY OF THE INVENTION

According to this invention, a primary or secondary alkyl halide, sulfate, or sulfonate is contacted with an alkali metal or alkaline earth metal hydroxide in the presence of both a catalytic amount of onium salt and a catalytic amount of carboxylate salt. This invention differs markedly from the prior art in numerous ways but most significantly in the use of a carboxylate salt catalyst in combination with an onium salt catalyst. The results of this combination are increased product yields and increased reaction rates at less rigorous process conditions.

DETAILED DESCRIPTION OF THE INVENTION

Primary or secondary alkyl or inertly-substituted alkyl halides, sulfates, or sulfonates are here used. By "inertly-substituted" is meant that the substituents on the alkyl moiety are unreactive to the instant process reagents or products under the instant process conditions. The number of carbon atoms in the molecule can vary widely but, where the alkyl moiety is wholly aliphatic, from 1 to about 18 carbon atoms are preferred. Representative alkyl compounds include: methyl, ethyl, propyl, butyl, isopropyl, neopentyl, octyl, dodecyl, octadecyl, etc.; inertly-substituted alkyl compounds include: allyl, benzyl, phenylethyl, phenylpropyl, phenylbutyl, and the like. The halides here used are chlorine, bromine, and iodine. Because of their familiarity and availability, allyl, benzyl, and alkyl chlorides and bromides are preferred.

The instant process also utilizes, as a reactant, an alkali metal hydroxide or alkaline earth metal hydroxide. Sodium and potassium hydroxide are preferred. Said hydroxides can be used in either dry or aqueous form. If aqueous, the solution can vary in concentration from a lower limit of 10 percent to an upper limit of about a saturated solution. However, best results are obtained at concentrations of from about 40 percent to about 60 percent.

The catalysts here used are carboxylate and thiocarboxylate salts. The anion moiety is either alkyl, aryl, arylalkyl, cycloalkyl, or an inertly-substituted anion thereof. Where the anion is wholly aliphatic, the number of carbon atoms will generally range from 1 to about 18, although there is no theoretical upper limit. While any suitable cation may be used, economy and familiarity make the alkali metals and alkaline earth metals preferable, with sodium and potassium especially preferable. By way of illustration, not limitation, these salts include: sodium, potassium and calcium acetate, propionate, butyrate, caprate, laurate, palmitate, stearate, cyclohexanecarboxylate, 3-chlorocyclohexanecarboxylate, benzoate, o-, m-, p-toluate, phenylacetate, o-, m-, p-chlorobenzoate, phthalate, salicylate, anthranilate, methoxybenzoate, oleate, linoleate, and the corresponding thiocarboxylate salts. Sodium acetate and sodium benzoate are preferred catalytic salts. Moreover, the skilled artisan will recognize that the above salts can be used per se, or they can be generated in situ by adding the corresponding acid to the basic reaction mixture.

The invention requires a catalytic amount of carboxylate or thiocarboxylate salt. Obviously, the amount will vary depending upon the chosen catalyst's efficiency under particular reaction parameters. In general, at least about 0.1 mole percent (and preferably about 1 mole percent) of carboxylate catalyst relative to the alkylating agent is required. Although no theoretical upper limit exists, reactor capacity, economics, and product purification suggest a general maximum of about 25 mole percent with preference for about 5 mole percent for best results.

The co-catalysts here used are quaternary ammonium salts and quaternary phosphonium salts having a carbon content of at least about 10 carbon atoms. These salts are known in the art as phase-transfer catalysts and are described in such publications as the *J. Am. Chem. Soc.*, 93, 195 (1971) and in British Patent No. 1,227,144 by Starks and Napier. The ammonium salts are currently preferred over the phosphonium salts and benzyltriethyl-, methyltri-n-butyl- and tetra-n-butylammonium chlorides, bromides and bisulfates are most preferred.

To further illustrate the type of onium salts used, suitable onium salts are presented by the formula

wherein: $Q^+$ is a quaternized atom of nitrogen or phosphorus, $R_1$-$R_4$ are hydrocarbyl groups, i.e. alkyl, aryl, alkylaryl, arylalkyl, cycloalkyl, etc., and $R_1$ can join with $R_2$, or $R_2$ with $R_3$, etc., to form a 5- or 6-membered heterocyclic compound having at least one quaternized nitrogen atom in the ring and may also contain one non-adjacent atom of nitrogen, oxygen or sulfur within the ring. Typically, $R_1$-$R_4$ are hydrocarbyl groups of from 1 to about 16 carbon atoms each with a combined minimum total of at least about 10 carbon atoms. The onium salts total carbon content generally does not exceed about 40 atoms, and preferably the carbon content does not exceed about 30 atoms.

The neutralizing anion portion of the salt, i.e., $A^-$ in the above generic formula, may be trimethylnaphthylammonium to convenience. Chloride and bromide are the preferred anions, but other representative anions include fluoride, iodide, tosylate, acetate, bisulfate, hydroxide, etc. The following compounds are illustrative: tetraalkylammonium salts, such as tetra-n-butyl-, tetrahexyl-, and trioctylmethyl-, hexadecyltriethyl-, and tridecylmethylammonium chlorides, bromides, iodides, bisulfates, tosylates, etc; arylalkylammonium salts, such as tetrabenzylammonium chloride, benzyltrimethyl-, benzyl-triethyl-, benzyltributyl-, and phenethyltrimethylammonium chlorides, bromides, iodides, etc; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethyl-naphthylammonium chloride, p-methylphenyltrimethylammonium chloride or tosylate, etc.; 5- and 6-membered heterocyclic compounds containing at least one quaternary nitrogen atom in the ring, such as N,N,N',N'-tetramethylpiperaziniumdichloride, N-methylpiperaziniumdichloride, N-hexylpiperazinium iodide, 4-pyridyltrimethylammonium iodide, N,N-dibutylmorpholinium chloride, N-octylthiazolium chloride, N-decylpyrrolium chloride, etc., and the corresponding phosphonium salts.

Like the carboxylate catalyst, the onium salt catalyst is also required in a catalytic amount and, like the carboxylate catalyst, this amount will vary depending upon the chosen catalyst's efficiency under particular reaction parameters. Generally, it has been found that best results are achieved when the onium salt catalyst is present in an amount from 0.1 mole percent (and preferably 1 mole percent) to about 25 mole percent (and preferably about 5 mole percent) relative to the alkylating agent.

The ratio of reagents here used can be any suitable ratio of alkylating agent and hydroxide ion. However, to maximize efficiency of the alkylating agent, the lower operative limit requires at least about two equivalents of hydroxide ion to alkylating agent. Practical considerations suggest a ratio of hydroxide ion to alkylating agent of about 4 to 1 as a preferred upper limit.

Temperature and pressure are not critical to the invention and thus can be selected as desired. Although preferred limits are governed by the specific choice and ratio of reagents, it has been found that generally temperatures between about 40° and about 100° C with atmospheric or autogenous pressure yield best results.

This invention can be conducted neat or in the presence of an inert organic solvent. For example, benzene, chlorobenzene, o-dichlorobenzene, methylene dichloride, etc. may be employed as solvents if desired.

The following examples are illustrative of certain specific embodiments of the invention. However, these examples are for illustrative purposes only and should not be construed as limitations upon the invention.

EXAMPLE 1

Preparation of dibenzyl ether

Benzyl chloride (12.6 g; 0.1 mole), a 50 percent aqueous solution of sodium hydroxide (35 g; 0.44 mole), tetra-n-butylammonium bisulfate (1.7 g. 0.005 mole), and sodium acetate (0.4 g; 0.005 mole) were added to a reaction vessel fitted with a thermometer and magnetic stirrer. The contents were then stirred and heated to 60° C. The reaction was slightly exothermic raising the temperature of the reaction mass to 63° C. The reaction mass was sampled at various intervals and the samples were analyzed by gas-liquid chromatography. The results are tabulated in Table I. Upon completion of the reaction, the reaction mass consisted of a lemon yellow organic layer, a heavy, caustic emulsion and solid sodium chloride on the flask bottom.

TABLE I

| Time (hr) | Percent Yield of ($\phi$CH$_2$)$_2$O* (%) |
|---|---|
| 0.5 | 34.3 |
| 1.5 | 84.6 |
| 3.0 | 98.7 |
| 19.0 | 100.0 |

*Based upon a theoretical yield calculated from gas-liquid chromatographic data.

EXAMPLE 2

Preparation of dibutyl ether

Butyl chloride (9.26 g; 0.1 mole), sodium hydroxide beads (3 g; 0.075 mole), a 50 percent solution of sodium hydroxide (50 g; 0.625 mole), sodium acetate (0.66 g; 0.008 mole), and tetra-n-butylammonium bisulfate (3.4 g; 0.01 mole) were added to a reaction vessel fitted with a thermometer and magnetic stirrer. The contents were stirred and heated to reflux. The refluxing reaction mixture stablized at 85°–90° C and was sampled at various intervals. The samples were analyzed by gas-liquid chromatography and gave the following results:

TABLE II

| Time (min) | Bu$_2$O (%) |
|---|---|
| 17 | 17.5 |
| 50 | 52.6 |
| 120 | 86.4 |
| 180 | 93.4 |

These results show that primary alkyl halides give comparable results to benzyl halides.

CONTROL A

Example 1 was repeated without sodium acetate. The results are tabulated in Table III.

TABLE III

| Time (hr) | Percent Yield of ($\phi$CH$_2$)$_2$O (%) |
|---|---|
| 0.5 | 11.2 |
| 1.5 | 18.6 |
| 2.5 | 28.0 |
| 19.0 | 54.0 |

Comparison of Example 1 and Control A results show the catalytic effect of the carboxylate salts. Both advantages of increased yield and reduced reaction time were obtained.

CONTROL B

Example 1 was repeated without the onium salt catalyst. The reaction mass was analyzed by gas-liquid chromatography. The results showed no reaction even after 2.5 hours. This indicates the necessity of having an onium salt present.

That which is claimed is:

1. A process for preparing symmetrical ethers comprising reacting by contacting a primary or secondary alkyl or inertly-substituted alkyl halide, sulfate, or sulfonate, with an alkali metal hydroxide or alkaline earth metal hydroxide in the presence of both a catalytic amount of a quaternary ammonium salt or a quaternary phosphonium salt of the formula $$R_1R_2R_3R_4Q^+A^-$$

wherein Q is a quaternized atom of nitrogen or phosphorus, A is a neutralizing anion, and $R_1$-$R_4$ are hydrocarbyl groups of from 1 to about 16 carbon atoms each with a combined minimum total of at least about 10 carbon atoms and a catalytic amount of a carboxylate salt or thiocarboxylate salt comprised of an alkyl, aryl, arylalkyl, cycloalkyl or inertly-substituted derivatives thereof, carboxylate or thiocarboxylate anion and an alkali metal or alkaline earth metal cation.

2. The process of claim 1 wherein the alkyl halide is a benzyl, allyl or alkyl chloride or bromide.

3. The process of claim 2 wherein the hydroxide is sodium or potassium hydroxide.

4. The process of claim 3 wherein the quaternary ammonium salt catalyst is tetra-n-butylammonium bisulfate.

5. The process of claim 1 wherein the carboxylate salt catalyst is sodium acetate or sodium benzoate.

6. The process of claim 1 wherein:
   a. both the quaternary ammonium salt catalyst and the carboxylate salt catalyst are present in an amount of at least about 0.1 mole percent relative to the alkylating agent,
   b. an aqueous solution of the alkali metal or alkaline earth metal hydroxide is present in a concentration from 10 percent to about a saturated solution, and
   c. the ratio of alkali metal hydroxide or alkaline earth metal hydroxide to alkylating agent is about 4 to 1.

7. The process of claim 6 wherein the quaternary ammonium salt catalyst is present in an amount from about 1 to about 25 mole percent relative to the alkylating agent.

8. The process of claim 6 wherein the carboxylate salt catalyst is present in an amount from about 1 to about 25 mole percent relative to the alkylating agent.

9. The process of claim 6 wherein the aqueous alkali metal or alkaline earth metal hydroxide is present in a concentration from about 40 to about 60 percent solution.

10. The process of claim 6 wherein the process is conducted at a reaction temperature between about 40° C and about 100° C under autogenous pressure.

11. The process of claim 10 wherein the process is conducted in the presence of an inert organic solvent.

12. The process of claim 11 wherein the inert organic solvent is benzene, chlorobenzene, o-dichlorobenzene or methylene dichloride.

* * * * *